US011461816B1

(12) United States Patent
Frens et al.

(10) Patent No.: US 11,461,816 B1
(45) Date of Patent: Oct. 4, 2022

(54) HEALTHCARE PROVIDER BILL VALIDATION

(71) Applicant: Red-Card Payment Systems, LLC, St. Louis, MO (US)

(72) Inventors: Jeremy L. Frens, Maryland Heights, MO (US); Patrick J. Coughlin, St. Louis, MO (US); Peter J. Hinden, Chesterfield, MO (US); Daniel M. Battista, St. Louis, MO (US)

(73) Assignee: Zelis Healthcare, LLC, Wilmington, DE (US)

( * ) Notice: Subject to any disclaimer, the term of this patent is extended or adjusted under 35 U.S.C. 154(b) by 216 days.

(21) Appl. No.: 16/839,961

(22) Filed: Apr. 3, 2020

Related U.S. Application Data

(63) Continuation-in-part of application No. 16/019,816, filed on Jun. 27, 2018, now Pat. No. 10,664,921.

(51) Int. Cl.
*G06Q 30/04* (2012.01)
*G06Q 40/08* (2012.01)
(Continued)

(52) U.S. Cl.
CPC ......... *G06Q 30/04* (2013.01); *G06F 16/2365* (2019.01); *G06F 16/258* (2019.01);
(Continued)

(58) Field of Classification Search
CPC ........ G06Q 30/04; G06Q 10/10; G06Q 20/14; G06Q 20/4014; G06Q 20/42; G06Q 30/0185; G06Q 40/08; G06Q 50/265; G06Q 20/102; G06Q 40/00; G06Q 10/00; G06Q 20/04; G06Q 20/02; G06Q 20/10; G06Q 20/18; G06Q 40/02; G06Q 20/20; G06Q 20/0425; G06Q 20/108; G06Q 20/40; G06Q 10/087; G06Q 20/351; G06Q 20/4018; G06Q 40/12; G06Q 99/00; G06Q 10/109; G06Q 20/322; G06Q 20/346; G06Q 20/382; G06Q 30/0202; G16H 40/20; G16H 10/60; G16H 40/67; G16H 15/00; G16H 70/20; G06F 16/258; G06F 16/2365;
(Continued)

(56) References Cited

U.S. PATENT DOCUMENTS

| 7,979,286 | B2 * | 7/2011 | Manning | G06Q 10/10 705/2 |
| 7,996,239 | B1 * | 8/2011 | Pellican | G06Q 10/10 705/2 |

(Continued)

*Primary Examiner* — Slade E Smith
(74) *Attorney, Agent, or Firm* — Nicholas Pfeifer; Smith & Hopen, P. A.

(57) ABSTRACT

A system for validation of healthcare provider bills includes obtaining an image of the bill on a mobile device which uses optical character recognition to resolve the patient identity, provider identity and amount due as alphanumeric characters. The system also receives adjudicated claims data from insurance companies in a non-standardized format. A claims conversion server converts the adjudicated claims data to a standardized machine-readable format. The standardized adjudicated claims data and provider bill are validated against each other in real-time so the patient can make payment in an accurate amount without having to first receive and decipher an EOB form.

20 Claims, 12 Drawing Sheets

(51) Int. Cl.
*G06Q 10/10* (2012.01)
*G06Q 20/40* (2012.01)
*G06Q 20/42* (2012.01)
*G06Q 50/26* (2012.01)
*G16H 10/60* (2018.01)
*G06Q 20/14* (2012.01)
*G06Q 30/00* (2012.01)
*G06F 16/25* (2019.01)
*G06F 16/23* (2019.01)
*G16H 40/20* (2018.01)
*G06V 30/414* (2022.01)

(52) U.S. Cl.
CPC ............. *G06Q 10/10* (2013.01); *G06Q 20/14* (2013.01); *G06Q 20/4014* (2013.01); *G06Q 20/42* (2013.01); *G06Q 30/0185* (2013.01); *G06Q 40/08* (2013.01); *G06Q 50/265* (2013.01); *G06V 30/414* (2022.01); *G16H 10/60* (2018.01); *G16H 40/20* (2018.01)

(58) Field of Classification Search
CPC ........ G06F 16/22; G06F 16/243; G06F 16/25; G06F 16/33; G06F 16/5846; G06F 16/909; G06F 16/93; G06F 40/205; G06F 40/279; G06F 40/295; G06K 9/00463; G06K 2209/01; G06K 9/00442; G06K 9/00449; G06K 9/00456; G06K 9/00469; G06K 9/00483; G06K 9/22; G06K 9/3258; G06K 9/6262; G07F 17/0014; G07F 7/1008; G06N 20/00; Y10S 707/99934; Y10S 707/99943
USPC .......................................................... 705/40
See application file for complete search history.

(56) References Cited

U.S. PATENT DOCUMENTS

| | | | | |
|---|---|---|---|---|
| 8,060,382 B1* | 11/2011 | Lee | G06Q 40/08 | 600/300 |
| 8,065,162 B1* | 11/2011 | Curry | G06Q 10/10 | 705/2 |
| 2001/0034621 A1* | 10/2001 | Kirsh | G06Q 40/08 | 707/999.107 |
| 2002/0007290 A1* | 1/2002 | Gottlieb | G06Q 30/06 | 705/4 |
| 2003/0191665 A1* | 10/2003 | Fitzgerald | G16H 50/20 | 705/2 |
| 2003/0195771 A1* | 10/2003 | Fitzgerald | G06Q 40/08 | 705/40 |
| 2004/0204960 A1* | 10/2004 | Wood | G06Q 10/10 | 705/2 |
| 2005/0033604 A1* | 2/2005 | Hogan | G06Q 20/14 | 705/40 |
| 2006/0047539 A1* | 3/2006 | Huang | G06Q 10/10 | 705/2 |
| 2006/0161463 A1* | 7/2006 | Poonnen | G06Q 40/08 | 707/999.01 |
| 2006/0265251 A1* | 11/2006 | Patterson | G16H 10/60 | 705/3 |
| 2007/0005402 A1* | 1/2007 | Kennedy | G06Q 40/08 | 705/3 |
| 2007/0005403 A1* | 1/2007 | Kennedy | G16H 40/20 | 705/3 |
| 2007/0050219 A1* | 3/2007 | Sohr | G06Q 40/08 | 705/4 |
| 2007/0194108 A1* | 8/2007 | Kalappa | G06Q 40/00 | 235/381 |
| 2007/0194109 A1* | 8/2007 | Harrison | G06Q 20/227 | 235/381 |
| 2007/0299699 A1* | 12/2007 | Policelli | G06Q 10/10 | 705/40 |
| 2008/0164305 A1* | 7/2008 | Ball | G06Q 10/10 | 235/375 |
| 2008/0172250 A1* | 7/2008 | Ambrose | G06Q 10/10 | 705/2 |
| 2009/0080408 A1* | 3/2009 | Natoli | G06F 16/258 | 370/351 |
| 2009/0138277 A1* | 5/2009 | Warren | G06Q 10/10 | 705/2 |
| 2009/0326974 A1* | 12/2009 | Tolan | G06Q 40/08 | 705/2 |
| 2010/0241595 A1* | 9/2010 | Felsher | G16H 10/65 | 707/E17.014 |
| 2011/0010189 A1* | 1/2011 | Dean | G06Q 40/12 | 705/2 |
| 2011/0099087 A1* | 4/2011 | Reinhardt, Jr. | G06Q 10/10 | 705/26.81 |
| 2011/0166883 A1* | 7/2011 | Palmer | G06Q 10/10 | 705/2 |
| 2011/0225006 A1* | 9/2011 | Manning | G16H 50/30 | 705/2 |
| 2011/0258001 A1* | 10/2011 | Green, III | G16H 40/20 | 705/3 |
| 2011/0258004 A1* | 10/2011 | Dean | G06Q 10/10 | 705/4 |
| 2012/0022887 A1* | 1/2012 | Chiappe | G06Q 30/04 | 705/2 |
| 2012/0239560 A1* | 9/2012 | Pourfallah | G06Q 20/102 | 705/40 |
| 2014/0343973 A1* | 11/2014 | Ruszala | G06Q 10/1057 | 705/4 |
| 2014/0379361 A1* | 12/2014 | Mahadkar | G06Q 40/08 | 705/2 |
| 2015/0006198 A1* | 1/2015 | Furr | G16H 40/20 | 705/2 |
| 2015/0120561 A1* | 4/2015 | Ver Hulst | G06Q 20/409 | 705/44 |
| 2016/0063201 A1* | 3/2016 | Allen | G06Q 10/10 | 705/2 |
| 2017/0351824 A1* | 12/2017 | DeGasperis | G06Q 20/102 | |
| 2019/0019574 A1* | 1/2019 | Byrnes | G16H 70/20 | |

* cited by examiner

HEALTHCARE PROVIDER BILL VALIDATION

CROSS-REFERENCE TO RELATED APPLICATIONS

This nonprovisional application is a continuation-in-part of and claims priority to nonprovisional application No. 16/019,816, entitled "Healthcare Provider Bill Validation and Payment," filed Jun. 27, 2018 by the same inventors.

BACKGROUND OF THE INVENTION

1. Field of the Invention

This invention relates to the healthcare industry. More specifically, it relates to the timely validation of a medical provider's bill.

2. Brief Description of the Art

The healthcare industry is plagued with issues corresponding to the timely distribution and clarity of what portion of a healthcare provider's bill is the patient's responsibility. As an example, an insured patient typically receives a healthcare provider's bill in the mail for some services that the provider rendered a month or so earlier. The healthcare provider's bill requires some payment, such as an amount of $100. However, at least part of the visit was presumably covered by insurance. The healthcare service provider likely submitted an 837 Health Care Claim. The insurance company receives a request for payment from the provider and the claim is adjudicated by the insurance company to determine what is covered by insurance versus what is the patient's responsibility. More specifically, the adjudicated claims data details the payment to that claim, including: what charges were paid, reduced or denied; whether there was a deductible, co-insurance, co-pay, etc.; any bundling or splitting of claims or line items; and to whom the payment is made.

A report called an explanation of benefits (EOB) is generated at some point following adjudication of the claim. A particular EOB form may not always align one-for-one with a specific 837 claim. It is not unusual for multiple EOBs to be generated in response to a single 837, or for one EOB to address multiple 837 submissions. Ultimately, the EOB information is important to healthcare providers for tracking payments received for services they provided and billed.

The problem is if the provider's bill (or "provider statement") arrives before the patient receives the EOB form, the patient has few options to know they are paying the correct amount. Often the patient simply discards the doctor's bill until the EOB form arrives and then waits for another round of billing from the doctor's office. Once the patient receives the EOB form, he or she must make certain that the EOB form is the correct one, which requires verifying a match between doctor, patient, date and services.

Even if the EOB form is the correct one, the patient must decipher the EOB information and match that against the amount the provider requested. If the patient cannot figure out how the amounts match, the patient might: (1) call the insurance company to discuss; (2) call the provider's office to discuss; (3) ignore the bill and see if another one comes in; (4) pay an amount believed to be correct; and/or (5) pay the bill then find out the insurance company also paid it thereby requiring the patient to seek reimbursement back from the provider.

In addition, EOB forms are often sent 2-4 weeks before the provider bills are received, or 2-4 weeks after, depending upon the insurance company. Therefore, they are out of synchronization. Moreover, EOB forms are often sent only once per month and grouped by patient. Therefore, finding the claims on an EOB form that the provider is billing for is not trivial. EOB forms further contain substantial amounts of information unrelated to the provider bill. The amount a provider requests to be paid is never known by the patient until the provider bill is compared to the EOB form.

These issues are even more exacerbated when a patient must visit many medical providers in different locations. The patient then receives a multitude of different bills at different times and may receive several EOB forms. In prior art systems, healthcare provider bills are stored locally in a format that is dependent on the hardware and/or software platforms in use in the provider's office. In addition, EOB data is often compiled and sent in a format that is determined by an insurance provider, which could also be dependent on the hardware and/or software platforms in use by the insurance provider. These systems make it is difficult to share information because of 1) non-standardized formatting; 2) different geographic locations; 3) lack of network connections; and 4) untimely distribution of information. Unfortunately, there is no system in place that can aggregate adjudicated claims data from a plurality of insurance providers, standardize the data, and automatically validate a healthcare provider's bill on behalf of a patient, so that the patient can timely and confidently issue payment without having to decipher unnecessary information provided in the EOB forms at some untimely date.

What is needed in the art is a system to timely synchronize and standardize the adjudicated claims data and validate the provider's bill, so the patient understands what to pay and has confidence he or she is paying the correct amount. However, in view of the art considered as a whole at the time the present invention was made, it was not obvious to those of ordinary skill in the field of this invention how the shortcomings of the prior art could be overcome.

BRIEF SUMMARY OF THE INVENTION

In an embodiment of the invention, a mobile device such as a smart phone is communicatively coupled to a remote network (typically the Internet through WIFI or cellular connections such as 3G, 4G, or 5G). The remote network would generally connect the mobile device to an application server hosted in a cloud computing platform or on-premise server. The mobile device has a processor, optical camera, memory and software that executes instructions to carry out the invention. The instructions take the form of a mobile app which is downloaded to the mobile device. A user of the mobile app stores his identity accessible through the mobile app. This may include his email address, a login username, password, healthcare member ID, payment information, and/or third-party authentication APIs (such as those available under the brands GOOGLE IDENTITY PLATFORM and FACEBOOK LOGIN).

A user of the mobile device (also referred to as "the patient") receives a healthcare provider bill and obtains a photographic image of the bill. This may be done from within the mobile app provided the mobile app has been granted access to the device's camera. Alternatively, a preexisting image in the image library of the mobile device may be selected from within the mobile app for processing. The image of the provider bill is sent to an OCR-processing engine. This may be done locally on the device using a software development kit (SDK) such as that sold under the brand ABBYY MOBILE OCR ENGINE and offered by ABBYY Software Ltd. out of Nicosia, Cyprus. Alternatively, the image may be transmitted to a remote OCR processing engine which resolves the alphanumeric characters and the context in which they appear on the bill. Yet another embodiment permits the end user to upload a digital file of the bill wherein the alphanumeric characters are readable by the software application directly (e.g., without OCR). The most common file format in this case is the Postscript Document Format (PDF) standard managed by Adobe Systems, Inc.

The OCR data from the bill is then extracted to sort through the mounds of unnecessary information such as advertisements, policy info, coupons, etc. The system identifies the text it found and in what location the text was located. To extract the proper data, the system looks for keywords and/or patterns. For example, the system may search keywords like "payment," "payments," "pmt" and then look for numerical values within a certain distance or at a certain relative location to identify the payment amount. The system may also look for only numerical values preceded by a dollar symbol. Likewise, the system searches the bill for the query terms "Date," "service date," or "svc date" and then searches for numerical, alphanumerical characters, and/or any values that have a date-like format within a certain distance or at a certain relative location to identify the date on which the services were rendered. The system performs this analysis to retrieve data from the unpaid bill for a predetermined dataset.

Some of the fields in the dataset that are read directly or resolved by OCR include: provider name, remit-to address, patient name, amount due, and patient account number. Service line data may also be read including dates of service, charge amounts, adjustments, CPT codes, service descriptions, insurance payment amount, and copay amounts.

When the healthcare provider initially serviced the patient, they sent a bill to an insurance carrier less any patient co-pay made at the time. The insurance company adjudicates the claim and determines what is covered by the insurance policy and what the patient must pay out-of-pocket. This information is reported to the system of the present invention in a non-standardized format. The system standardizes the data using OCR or predetermined extraction program. The standardized adjudicated claims data is then stored in an EOB database. The standardized adjudicated claims data and text data from the provider bill is then compared by a string comparison function (herein "Red Card Engine") which looks to match fields such as the provider name, remit-to address, amount due, patient name, patient account number, service line data and the like. If standardized adjudicated claims data is linked to the provider bill, then the amounts can be reconciled and determined if accurate and should be paid. An important utility of this invention is the temporal synchronization of both the standardized adjudicated claims data and patient bill. Typically, this information is received by the patient in a staggered fashion and the patient is unsure whether to pay what the provider is requesting or not.

In the event a match cannot be immediately made, the name, address and other identifying information of the provider may be used to query "near matches" which can then be presented to the user on the mobile device to confirm which healthcare provider was seen. Yet another embodiment of the invention geolocates the patient while they are at the provider's office during the visit for which the bill is later generated. This provides both location data and a date/timestamp for the visit itself. This information is stored and later retrieved to match the correct standardized adjudicated claims data to the provider bill. The mobile app may run in the background and periodically poll location data to determine whether the device is at a location where healthcare service is provided. The user may also open the mobile app and simply confirm manually the location they are in.

The mobile app may also store or access a plurality of payment methods which can be authorized to pay the healthcare provider directly from the mobile app. The patient may pay in full by one payment means, pay a portion of the bill, spread payments over time, and/or use multiple payment means to pay all or a portion of a provider bill. Payment means may include ACH draws on a patient bank account, payment cards, health savings accounts (HSA), flexible spending account (FSA) and the like. In the event of a discrepancy between the amount billed by the provider as "patient responsibility" and that noted by the standardized adjudicated claims data as "patient responsibility" the mobile app may present both amounts and let the user pay either one. An advantage of this method is that the patient may pay the "lesser amount not in dispute" so the healthcare provider at least gets a substantial portion of the amount billed while both parties sort out any mistakes in the billing process. This is superior to forcing a stalemate wherein the patient cannot easily execute a payment when the amounts do not align. By reducing the user interaction with the mobile app user interface (e.g., presenting anticipated payment solutions for authorization), friction is reduced in the payment process. Healthcare providers are paid faster, and patients have greater certainty and confidence in the billing process.

Yet another feature of the present invention is tracking costs for treatments and procedures. Current Procedural Terminology (CPT) is a medical code set that is used to report medical, surgical, and diagnostic procedures and services to entities such as physicians, health insurance companies and accreditation organizations. CPT codes are made up of five characters. These characters are numeric and alphanumeric depending on which category the CPT code falls in. CPT codes are submitted by the healthcare provider to the insurance carrier for payment. The CPT codes are matched to fee schedules by the insurance companies to determine how much of the healthcare provider's bill is covered under a given insurance policy. The remainder is the responsibility of the patient. Because the present invention has access to thousands of adjudicated claims and provider statements, it is possible for the mobile device to present statistical data on the average cost for a given CPT code including what the average patient responsibility is. This may prove useful for the patient if the procedure cost substantially deviates over the averages for a given area. Alternatively, the average cost for a CPT code may help the healthcare provider substantiate the billing and assure the patient that the costs are in line with what other patients experience.

Another feature of the present invention is aggregating a history of the procedures for a given healthcare provider along with historical billing. Access to this and other records on the mobile app may be shared with family members and authorized healthcare providers. The mobile app may also query for provider ratings including billing, effectiveness, timeliness and the like.

An embodiment of the present invention includes a method of standardizing healthcare records to analyze the validity of a healthcare provider's unpaid bill. The method includes providing remote access to insurance providers over a first network so any one of the insurance providers can provide adjudicated claims data to a claims conversion server. The insurance providers provide the adjudicated claims data in a non-standardized format dependent on the hardware or software platform used by the one of the insurance providers.

To account for the non-standardized formats across insurance companies, the system uses a claims conversion server to convert the non-standardized adjudicated claims data into a standardized format. In an embodiment, the standardized adjudicated claims data is stored in an EOB database in the standardized format.

The system also provides remote access to users over a second network so any one of the users can upload the healthcare provider's unpaid bill through a graphic user interface on a patient's mobile device. The system automatically identifying the identity of the user that uploads the healthcare provider's unpaid bill. The one user's identity is identified by one or more of a name, a social security number, a date of birth, or a zip code either on the bill or taken from the user's subscription account to use the described services.

A bill validation module is then initiated. The bill validation module executes the following steps: automatically identifying from the healthcare provider's unpaid bill a medical provider's identity, an amount due, and a service date; automatically accessing the EOB database and performing a scoring algorithm to determine if any of the standardized adjudicated claims data in the EOB database contains enough similarities to the one user's identity, the medical provider's identity, the amount due, and the service date to exceed a predetermined scoring threshold. In an embodiment, the system also compares the billed amount to the EOB data during the validation procedure.

If one of the standardized adjudicated claims data exceeds the predetermined scoring threshold, the system automatically generates a message containing a confirmation that the healthcare provider's unpaid bill has been validated. The message is then transmitted to the user over the second network, so that the user has immediate access to up-to-date payment information. In an embodiment, the user is provided with an option to initiate a digital payment to the medical provider on the user's mobile device.

An embodiment also includes displaying on the user's mobile device a comparison of the amount of the healthcare provider's unpaid bill that the user is required to pay as calculated by the healthcare provider and the amount of the healthcare provider's unpaid bill that the user is required to pay as reported by standardized adjudicated claims data. The system may further display a selectable control to pick whether to pay the amount of the healthcare provider's unpaid bill as calculated by the healthcare provider or the amount of the healthcare provider's unpaid bill that the user is required to pay as reported by standardized adjudicated claims data.

An embodiment includes a step of receiving the healthcare provider's unpaid bill as a first digital image taken with a digital camera and converting the first digital image to a digital dataset of alphanumeric characters. In an embodiment, the digital dataset includes the medical provider's identity, the amount due, and the service date.

An embodiment includes automatically generating a message containing an explanation that the healthcare provider's unpaid bill has not been validated by the standardized adjudicated claims data if none of the standardized adjudicated claims data exceeds the predetermined scoring threshold. That message is transmitted to the user over the second network, so that the one user has immediate access to up-to-date payment information.

An embodiment of the present invention includes a method of standardizing healthcare records to analyze the validity of a healthcare provider's unpaid bill. The method includes providing remote access to insurance providers over a first network so any one of the insurance providers can provide adjudicated claims data to a claims conversion server. The insurance providers provide the adjudicated claims data in a non-standardized format dependent on the hardware or software platform used by the one of the insurance providers.

To account for the non-standardized formats across insurance companies, the system uses a claims conversion server to convert the non-standardized adjudicated claims data into a standardized format. In an embodiment, the standardized adjudicated claims data is stored in an EOB database in the standardized format.

The method further includes receiving a first digital image of the healthcare provider's unpaid bill taken with a digital camera and digitally sent from a patient's mobile device. The first digital image is then converted to a digital dataset of alphanumeric characters. The digital dataset includes a healthcare provider's identity, an amount due, and a service date.

A patient's identity is determined, and a bill validation module is initiated. The bill validation module executes the following steps: automatically identifying standardized adjudicated claims data that corresponds to the patient's identity; automatically matching the digital dataset of the healthcare provider's unpaid bill to a claim in the retrieved standardized adjudicated claims data that corresponds to the patient's identity; automatically validating the amount due listed on the healthcare provider's unpaid bill by comparing the amount due listed on the healthcare provider's unpaid bill against an amount that the patient must pay out-of-pocket provided in the matched claim. In an embodiment, the patient's identity is identified by one or more of a name, a social security number, a date of birth, or a zip code.

In response to validating the amount due listed on the healthcare provider's unpaid bill, a message that contains a confirmation that the healthcare provider's unpaid bill has been validated is automatically generated. The message is then transmitted to the patient, so that the patient has immediate access to up-to-date payment information.

An embodiment includes providing, on a graphic user interface, the patient with an option to initiate a digital payment to the healthcare provider.

An embodiment includes displaying on the patient's mobile device a comparison of the amount of the healthcare provider's unpaid bill that the patient is required to pay as calculated by the healthcare provider and the amount of the healthcare provider's unpaid bill that the patient is required to pay as reported by the standardized adjudicated claims data. An embodiment includes displaying a selectable control to pick whether to pay the amount of the healthcare provider's unpaid bill as calculated by the healthcare provider or the amount of the healthcare provider's unpaid bill that the patient is required to pay as reported by standardized adjudicated claims data. An embodiment provides the patient with the option to pay an amount of the patient's choosing.

An embodiment includes, responsive to none of the standardized adjudicated claims data matching the digital dataset, automatically generating a message containing an explanation that the healthcare provider's unpaid bill has not been validated by the standardized adjudicated claims data.

The message is transmitted to the one user, so that the one user has immediate access to up-to-date payment information.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF AN EMBODIMENT

The present invention includes a network-based healthcare bill management system that collects, converts, and consolidates adjudicated claims data from various insurance companies and bills from various healthcare providers. The adjudicated claims data is converted into a standardized format and is stored in a network-accessible database. Likewise, the bills from various healthcare providers are converted into a standardized format and specific datasets of information are extracted. The system automatically determines whether the bill is valid in comparison to the standardized adjudicated claims data in real time. The validation occurs well in advance to when EOB forms are typically provided to patients and eliminates the need for a patient to try to decipher the immense and usually ambiguous data supplied in these forms. Furthermore, the system immediately generates a message as to whether the bill is validated, and the message is transmitted over a network to the patient. The patient is then provided with an opportunity to immediately initiate a digital payment to the healthcare provider.

Figure 1:
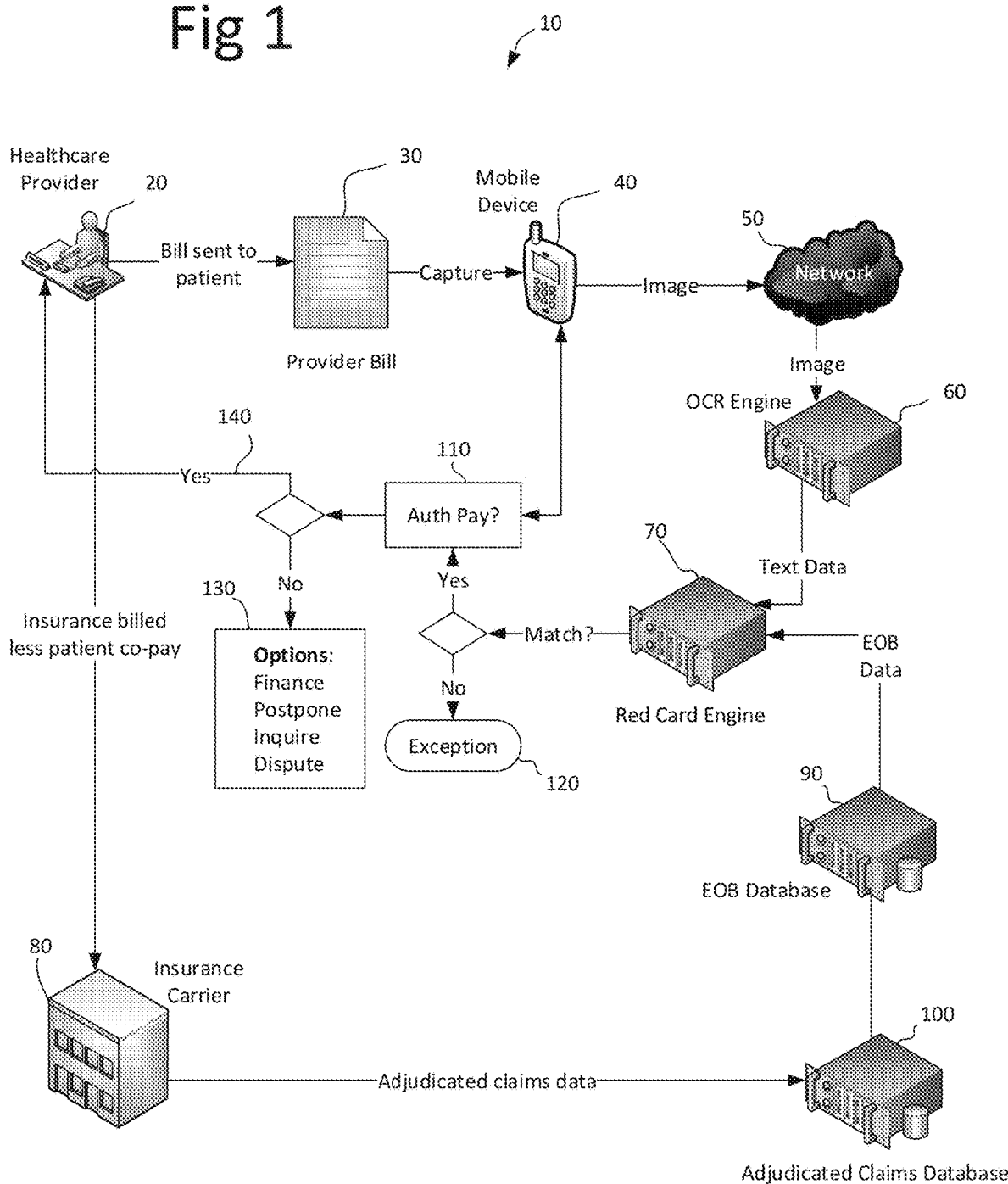
FIG. 1 is a diagrammatic view of an embodiment of the invention using remote OCR.

The novel invention is denoted as a whole in FIG. 1 by the reference numeral 10.

Healthcare provider 20 treats a patient and sends a claim to an insurance company. The term "insurance provider" includes insurance companies, health maintenance organizations (HMOs), preferred provider organizations (PPOs), third party administrators (TPAs) or government agencies such as Medicare, Medicaid, etc. The claim is typically in an EDI 837 transaction set which was established to meet HIPAA requirements for the electronic submission of healthcare claim information. The claim information includes: a description of the patient, the patient's condition for which treatment was provided, the services provided, date of service, and the cost of the treatment. The claim is received by insurance company 80 who adjudicates the claim and generates adjudicated claims data in a format dependent on the hardware and/or software platform used by the insurance provider. The adjudicated claims data is stored in adjudicated claims database 100. The adjudicated claims data is subsequently supplied to EOB database 90.

Figure 12:
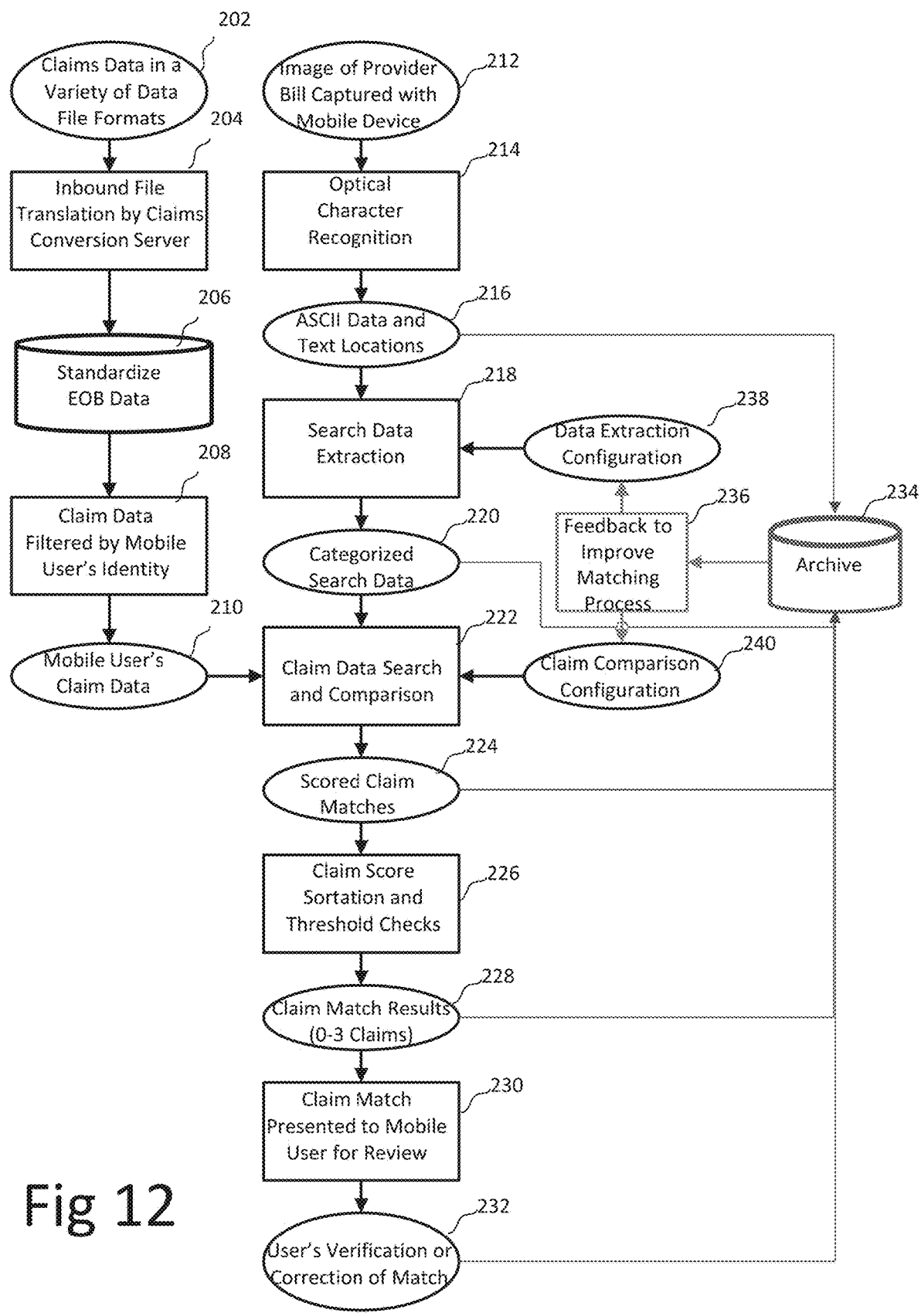
FIG. 12 is a flowchart of an embodiment of the present invention.

However, the adjudicated claims data provided by insurance companies can be provided in many different formats and file types (FIG. 12, 202). In other words, the adjudicated claims data is provided in a non-standardized format dependent on the hardware and/or software platform used by the insurance provider. These non-standardized formats can include but are not limited to, PDF, binary, or text file. The present invention uses a claims conversion server to standardize the adjudicated claims data (FIG. 12, 204). The standardized adjudicated claims data is referred to as "standardized EOB data" or "standardized adjudicated claims data." The standardized EOB data is stored in EOB database 90. In an embodiment, the standardized EOB data is stored in a relational data format and is machine readable, rather than human readable.

The adjudicated claims data provided by insurance companies may include a variety of different information 102, 104. Typically, there are commonalities in the provided information across insurance companies. The typical commonalities in adjudicated claims data across different insurance companies includes user identification, dates of service, patient acct number, amount charged, discount amount, and patient responsibility. In converting the adjudicated claims data into a standardized format, an embodiment of the present invention records only a subset of information in a standardized format. In an embodiment, the subset of information includes provider name, dates of service, patient identity, patient responsibility, total charge, and discount amount. In an embodiment, patient identity is captured by one or more of patient name, SSN, DOB, zip code, first name, and last name. In an embodiment, this subset of data is stored in a machine-readable relational database.

The adjudicated claims data is standardized using OCR or predetermined extraction program to extract data and then compile that data into a standardized format, such as a machine-readable relational database. When using a predetermined extraction programs, the system relies on a consistent formatting for each insurance company. The predetermined extraction programs use relational spacing to extract information located at specific locations on the files provided by the insurance companies. As long as a particular insurance company uses its own consistent format for transmitting non-standardized adjudicated claims data, the predetermined extraction program designed for that particular insurance company will extract the same dataset each time. That data is then standardized and stored in the EOB database 90.

In an embodiment, insurance companies can connect to adjudicated claims database 100 and/or EOB database 90 to manipulate the information in the database. In an embodiment, the system performs aggregation steps to organize the data in the databases based on insurance companies, healthcare providers, and/or patient identities.

At some point, healthcare provider 20 sends healthcare provider bill 30 to the patient. Using mobile device 40, the patient captures an image of healthcare provider bill 30 (FIG. 12, 212), which is transmitted over network 50 (e.g., Internet) to OCR engine 60 (FIG. 12, 214). OCR engine 60 converts the image into text data which is then received by Red Card Engine 70 (FIG. 12, 216-218). In an embodiment, the bill is converted to text on the user's device prior to being transmitted over a network to Red Car Engine 70. Some of the fields converted to text by OCR from the provider bill include provider name, remit-to address, patient name, amount due, patient account number, dates of service, charge amounts, adjustments, CPT codes, service descriptions, insurance payment amount and copay amounts.

Once the image has been converted to text, Red Card Engine identifies the various text values for various query terms (FIG. 12, 220). A query term is the search term and the text values are the term(s) that identify the particular value for each search. For example, "patient name" may be the query term while the patient's actual name, e.g., "John Doe" is the text value. An embodiment may seek text values corresponding to the following query terms: provider name, remit-to address, patient name, amount due, patient account number, dates of service, charge amounts, adjustments, CPT codes, service descriptions, insurance payment amount and copay amounts.

In an embodiment, Red Card Engine 70 uses relative spatial analysis to determine text correlations when extracting data from the healthcare provider's bill. In an embodiment, Red Card Engine 70 looks to text values immediately following, immediately below, or within a predetermined distance from each query term. The distance may be measured using pixels and the predetermined threshold may be a certain number of pixels. The distance may also be measured based on a percentage of the image's size, which allows the system to work correctly over a wide range of camera resolutions. In an embodiment, the distance is measured using any other know method for digitally determining the distance between text or other digital objects.

In an embodiment, Red Card Engine 70 first considers text values immediately following each query term, then considers text values immediately below each query term, and then considered text values within a predetermined distance from each query term. For example, if Red Card Engine 70 is trying to determine the patient's name for a particular bill the query term may be "patient name" and the system looks for text values immediately following "patient name" on the same text line. If the text "John Doe" immediately follows the query term "patient name" then the system records "John Doe" as the patient's name. If, however, there are no text values immediately following "patient name" on the same text line, the system determines if there are any text values immediately below the query term "patient name." If there are no text values immediately below the query term, the system looks for any terms within a predetermined distance from the query term. Thus, the system is able to account variations in organizational displays on healthcare provider bills.

In an embodiment, Red Card Engine 70 looks for unique patterns or symbols. For example, the system may search keywords like "payment," "payments," "pmt" and then look for numerical values preceded by a dollar symbol. Likewise, the system searches the bill for the query terms "Date," "service date," or "svc date" and then searches for numerical or alphanumerical characters values that have a date-like format to identify the date on which the services were rendered. The system performs this analysis to retrieve data from the unpaid bill for a predetermined dataset.

When the bill has been converted to text and the text values have been extracted for the various query terms in a particular dataset, Red Card Engine 70 performs string-handling routines to match up the standardized EOB data received from EOB database 90 with the text data extracted from OCR Engine 60 (FIG. 12, 222). Some common fields for comparison include dates of service, patient responsibility, total charge, discount amount, provider name, remit-to address, amount due, patient name, and/or patient account number. In an embodiment, at least patient identity; dates of service, patient responsibility, total charge, and discount amount are compared. In an embodiment, user identification, dates of service, patient account number, amount charged, discount amount, patient responsibility, and provider name are compared between the standardized EOB data and the extracted text from the healthcare provider's bill.

As depicted in FIG. 12, an embodiment includes Red Card Engine 70 first identifying a patient's name on the healthcare provider's bill after the bill has been converted to machine readable text or through the account of the user that submitted the bill (208). Red Card Engine 70 then analyzes the standardized EOB data in EOB database 90 to determine if there is any data corresponding to the identified patient. Patient identity may be identified by patient name, member ID, SSN, DOB, zip code, first and last name. The system then considers only the standardize EOB data corresponding to the patient's identity (210).

If Red Card Engine 70 cannot match the bill to standardized EOB data based on patient identification methods, an embodiment searches for matches for the total amount charged, amount due, healthcare provider's identity and/or date of service. Red Card Engine 70 may further compare other fields identified in the preceding paragraph to increase the likelihood of a match between the healthcare provider's bill and the standardized EOB data. An embodiment looks for matches for patient identity along with total amount charged, amount due, healthcare provider's identity and/or date of service.

An embodiment further considers whether a date of service falls within a date range provided in the standardized EOB data. EOB data is often a collection of several claims having occurred within a predetermined date range, e.g., 1 month. Thus, the system may be unable to match an exact date and could thus consider whether the date of service on the bill lands within a date range provided in the standardized EOB data.

An embodiment also includes one or more quantitative matching thresholds for determining if the bill is validated, more information is need, or the bill is not valid. The system calculates a total claim score based on the number of fields of comparison that are matched between the healthcare provider's bill and the standardized EOB data (FIG. 12, 224). The fields for comparison may have uniform weight values or may have different weighted values based on the uniqueness of each field of comparison. For example, a match of the user's SSN may be weighted more than a match of the healthcare provider's name. The greater the matching score, the more likely that the healthcare provider's bill is matched to a claim based on the standardized EOB data.

In an embodiment, there may be several quantitative matching thresholds. The system uses matching scores to sort through multiple matches if the provider's bill is matched to several different service dates/different claims (226). In an embodiment, the top three claim matches are sorted from the rest. (228). The matches are then sent to the user over a network and displayed to the user on a graphic user interface (230). In an embodiment, the user is provided with an option to identify which claim corresponds to the bill be analyzed.

In an embodiment, the system only advises making a payment when a minimum quantitate matching threshold has been met. For example, if there is a 95% match between the healthcare provider's bill and the standardized EOB data, the system notifies the user of a positive match and presents the user with an option to digitally pay the healthcare provider.

In an embodiment, when the standardized EOB data and provider bill are matched, they are presented concurrently to the patient on the mobile device 40. These two separate but related files convey to the patient their financial responsibilities with an enhanced level of validity. Because the provider bill and standardized EOB data were previously received out of sequence, it was difficult for a patient to confidently make timely payment on the patient responsibility of the provider bill. When matched, the patient authorizes payment 110 through mobile device 40 which sends funds 140 to healthcare provider 20. Alternatively, the patient may not authorize payment in which mobile device 40 presents additional options 130 including: financing the provider bill; postponing payment on the bill; inquiring from either the insurance carrier or provider about the bill; and/or disputing the bill. Alternatively, the patient may pay the bill separately, outside of the app.

Figure 4:
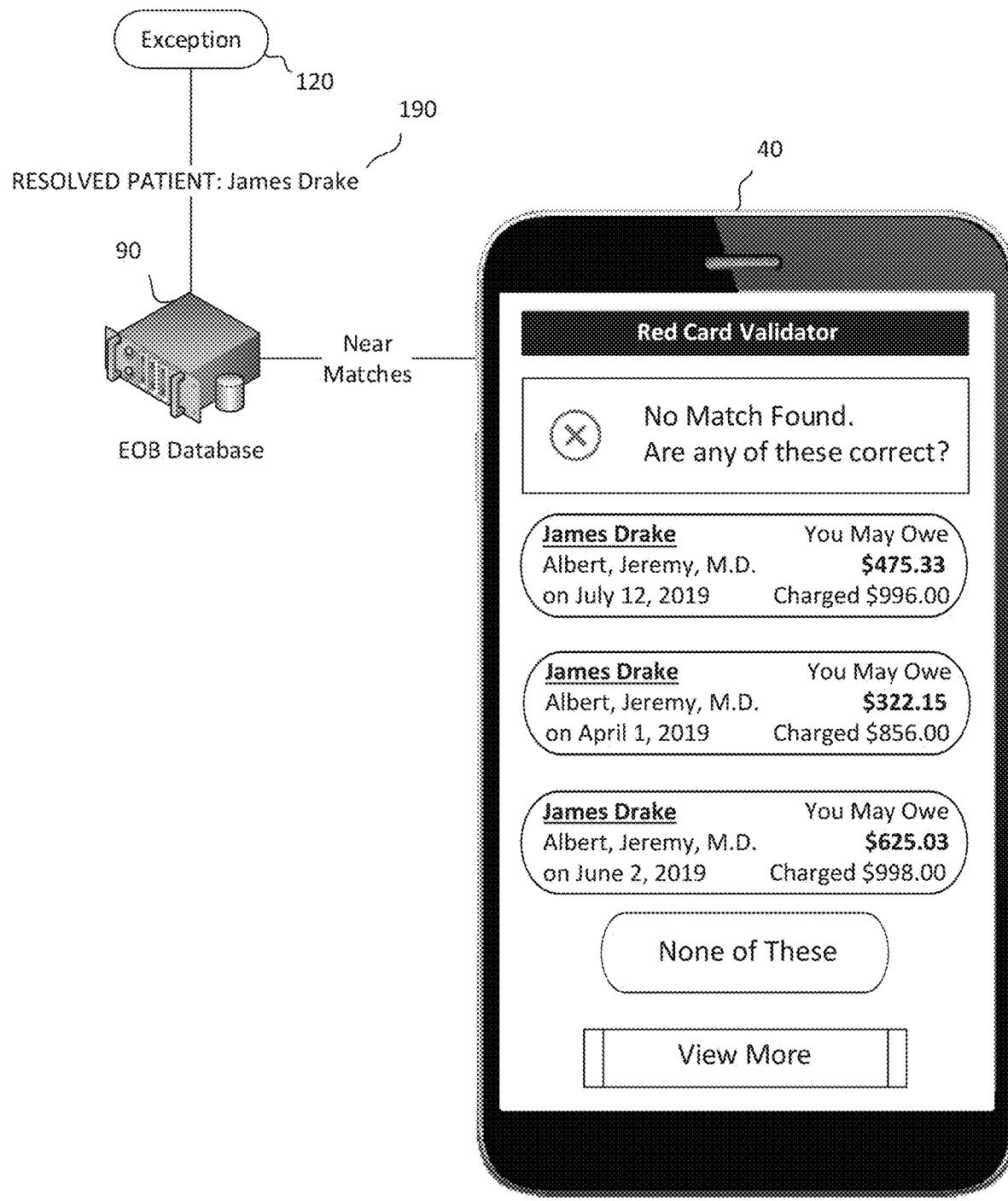
FIG. 4 is a partially diagrammatic, partial GUI showing an exception handling procedure according to an embodiment of the invention.

In the event a match is not made between standardized EOB data and text data from provider bill 30, or a certain threshold score is not met, an exception 120 is thrown. Additional querying may take place including comparing more fields between provider bill 30 and standardized EOB data. Such additional fields may include service line data such as: dates of service; charge amounts; adjustments; CPT codes; service descriptions; insurance payment amount; and copay amounts. If a match can still not be found, then near matches may be presented to the mobile device 40 user. Such a process is shown in FIG. 4 wherein the resolved patient string 190 was "James Drake." This string is processed against EOB database 90 which produces near matches and displays them on mobile device 40. The end user of mobile device 40 may simply select with a single touch the correct claim.

When matches are not made, the system can provide a user with a message or non-textual indicators, such as a red light or stop sign to inform the user that there is some incorrect information. The system may also send a question mark to a user to indicate that there is no match. The system may send to the user possible reasons as to why a match was not achieved to help guide a user to correcting the issue. In a certain embodiment, a user is provided with an option to digitally request that a third party negotiate a diminished payment or a payment plan.

An embodiment includes an algorithm to periodically recheck the EOB database to see if additional EOB data is stored that better matches the unpaid bill if a match is not initially found. If a match is eventually received, the system automatically notifies the user.

An embodiment also includes providing the user with the option to verify which of several matched claim is correct or verify if the match is incorrect (232). The embodiment may also archive user responses (234) and use the responses as feedback to improve the matching algorithm through machine learning (236). The feedback loop may reinitiate the step of extracting data from the healthcare provider's bill (238) and/or reinitiate the step of comparing the healthcare provider's bill with the standardized EOB data (240).

Figure 5:
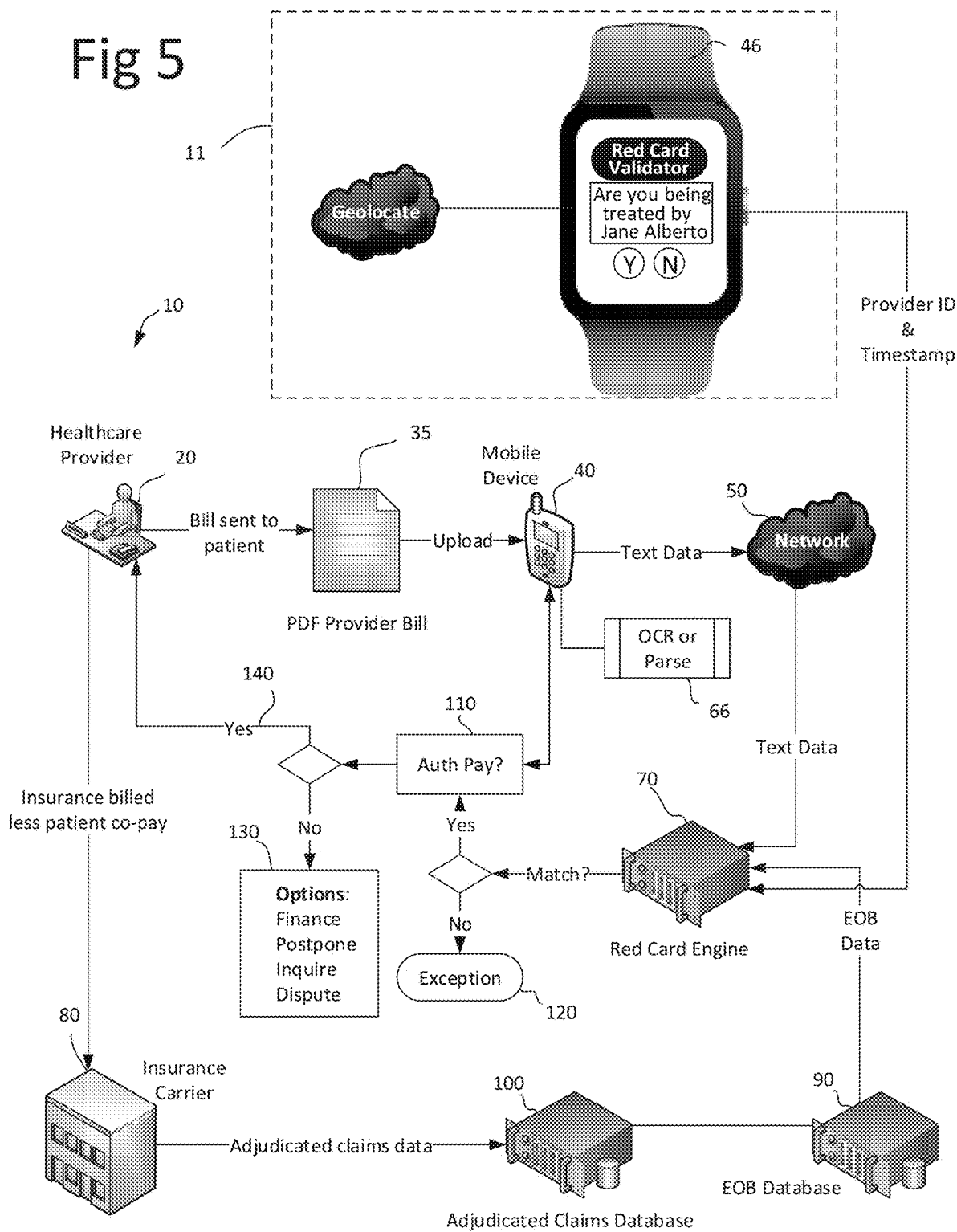
FIG. 5 is a partially diagrammatic, partial GUI showing geolocation used to help match a provider bill to an EOB according to an embodiment of the invention.

Yet another embodiment of the invention polls the location of the mobile device user when they originally visited healthcare provider 20. This is illustrated in FIG. 5 with a smartwatch 46 embodiment of the mobile application which geolocates 11 the end user during the visit to the provider. The geolocation process 11 may comprise a plurality of geo-fenced providers so that merely arriving at the location of the provider triggers a log to be generated with the provider identity and timestamp. The trigger may be upon arrival or could include a set threshold requiring the end user to be within the geo-fence for a predetermined period of time. This helps avoid false positives in the event the end user is simply passing through various medical practices on their way to healthcare provider 20. The provider ID and timestamp are used by Red Card Engine 70 to match the provider bill 30 and the standardized EOB data.

Figure 2:
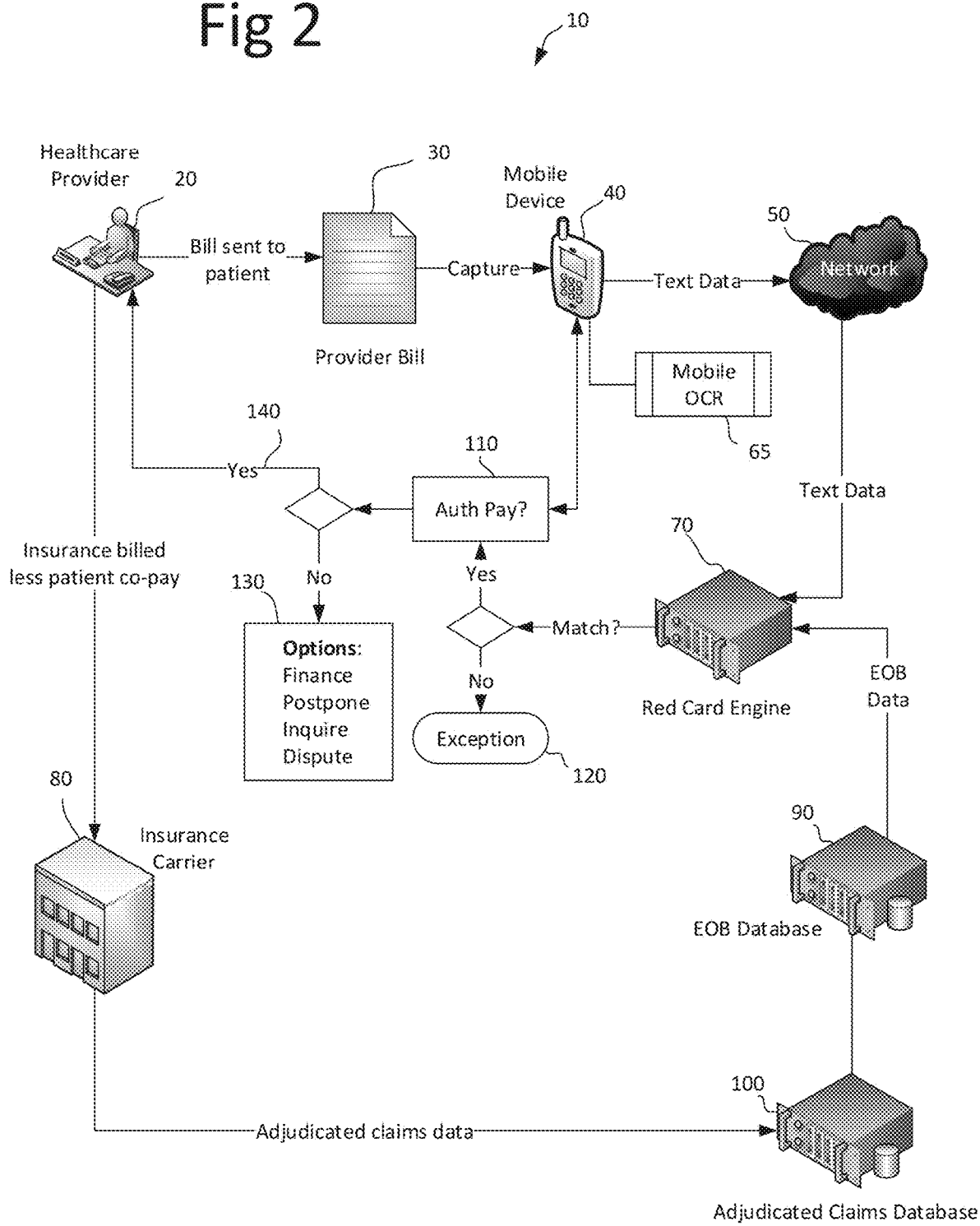
FIG. 2 is a diagrammatic view of an embodiment of the invention using local OCR on the mobile device.

FIG. 2 shows an alternative embodiment of the invention wherein a mobile OCR SDK 65 is integrated into the mobile app running on mobile device 40 so that the image-to-text processing of provider bill 30 occurs locally instead of remotely. Accordingly, text data is passed through network 50 and then directly to Red Card Engine 70 for matching with EOB data from adjudicated claims database 100.

Figure 3:
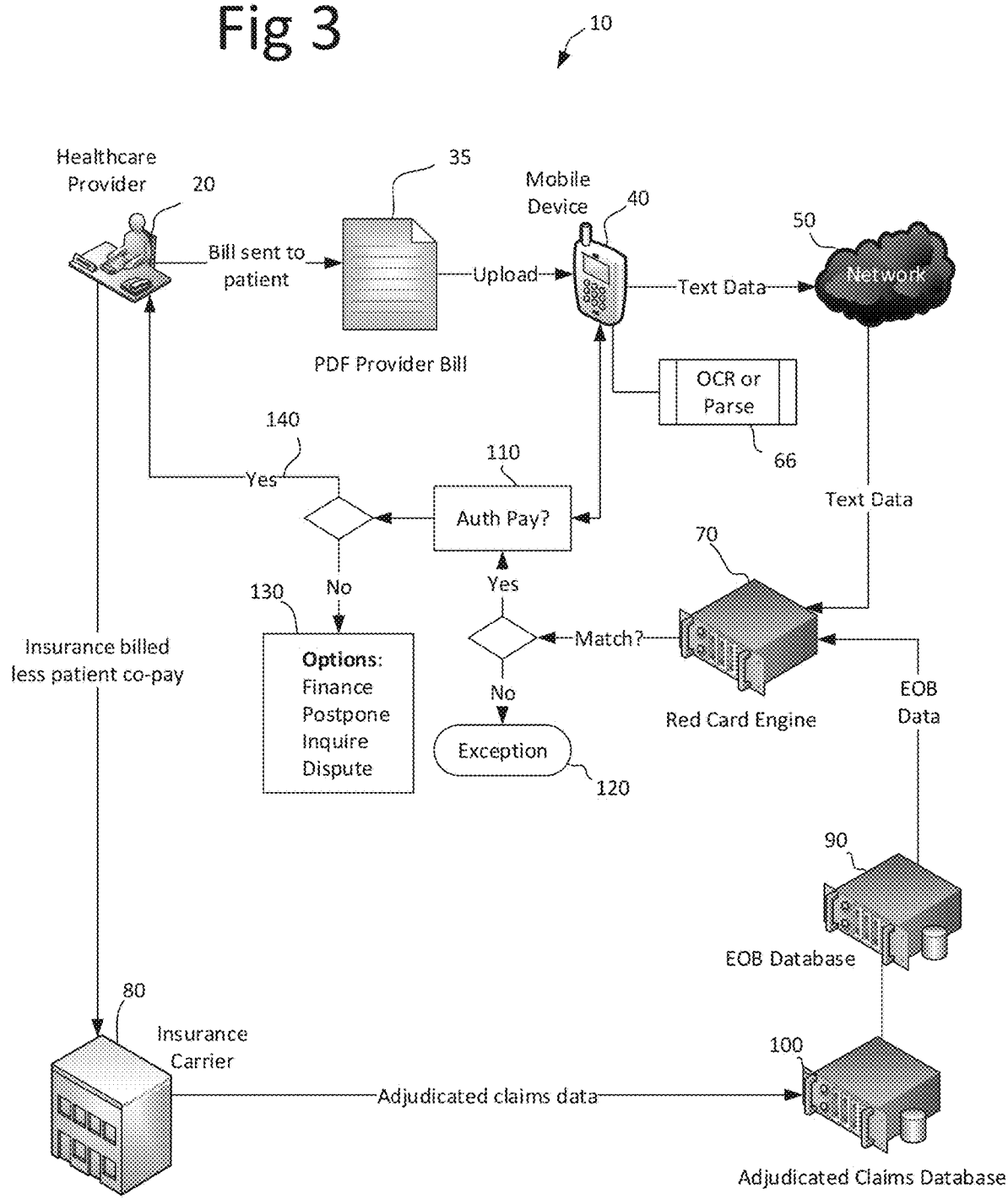
FIG. 3 is a diagrammatic view of an embodiment of the invention wherein the provider bill is uploaded rather than imaged.

In yet another embodiment of the invention shown in FIG. 3, no OCR is required as provider bill 35 is a digital file wherein the text encapsulated within is directly readable without any OCR process. The most common format for such digital documents is the PDF standard.

Figure 6:
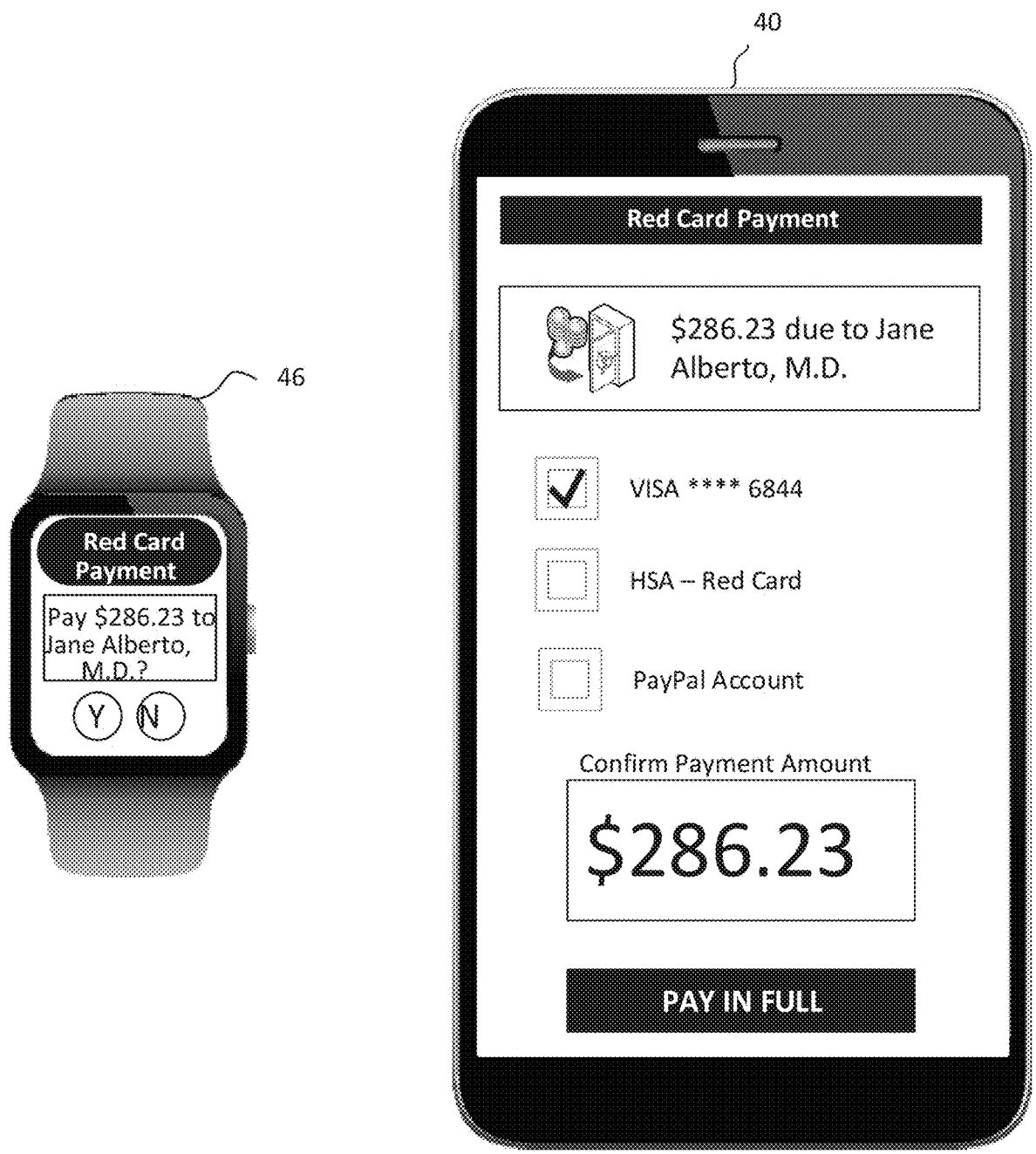
FIG. 6 shows two device GUIs for making payment on a provider bill according to an embodiment of the invention.
Figure 7:
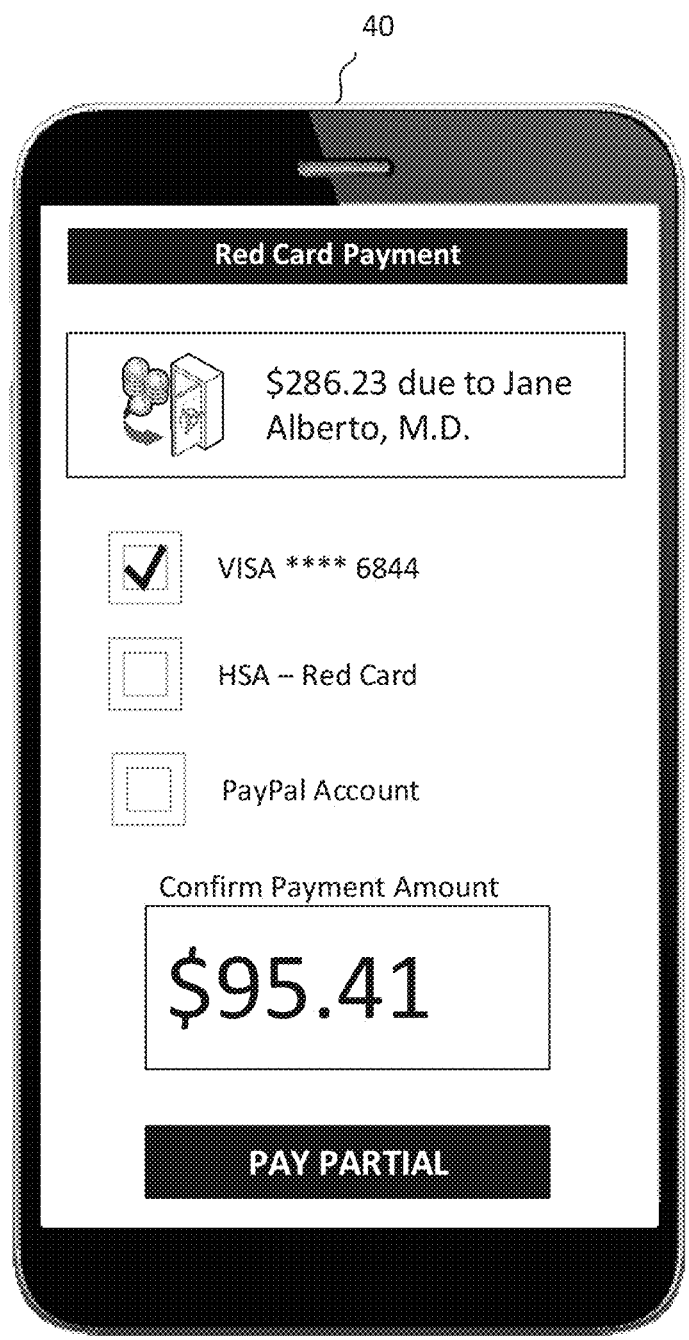
FIG. 7 shows a device GUI enabling partial payment according to an embodiment of the invention.
Figure 8:
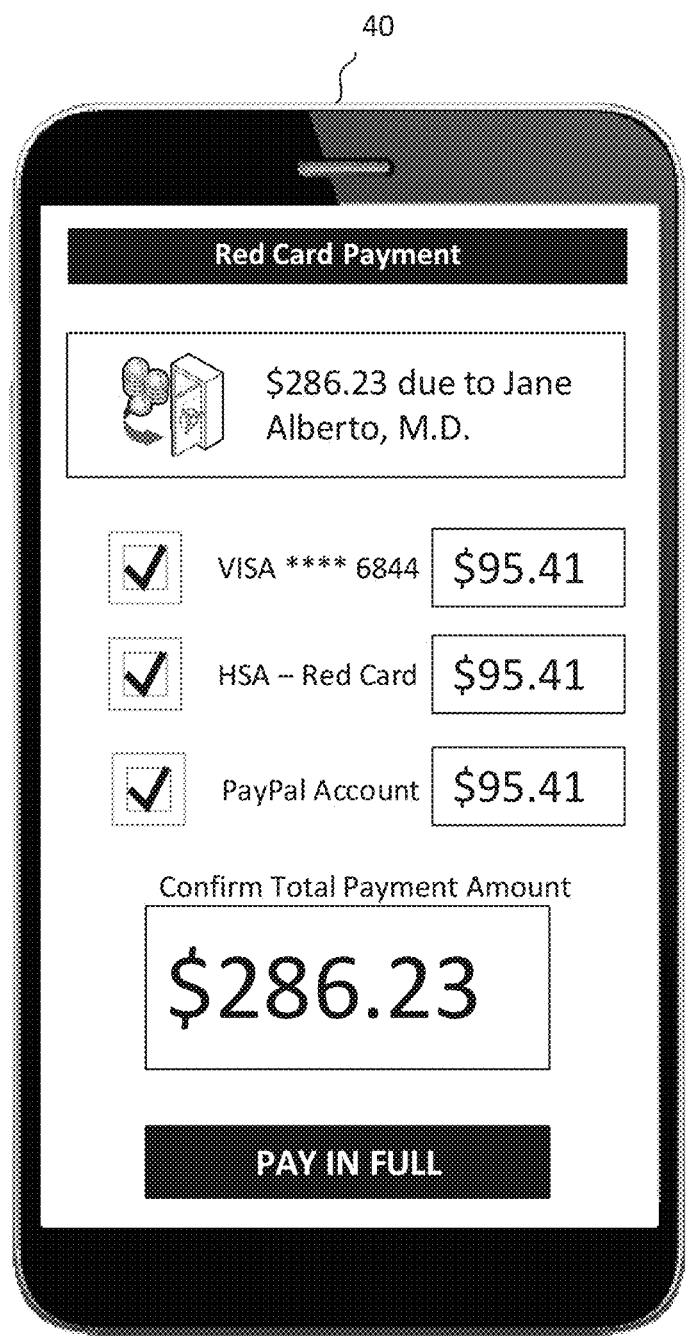
FIG. 8 shows a device GUI enabling payment from multiple sources according to an embodiment of the invention.

In FIG. 6, a plurality of payment methods is stored in the mobile device 40 app including a VISA payment card, an HSA savings account and a PAYPAL account. A companion smartwatch app 46 also displays a payment authorization UI. The end user may select the healthcare provider name to open another screen with additional details about the billing and EOB information. The end user may specify the exact amount to be paid but generally the payment textbox control will populate with the default amount in agreement between the provider bill and the EOB. FIG. 7 shows payment of a portion of the full amount to the healthcare provider. FIG. 8 shows payment in full but split between three different payment sources. Because the mobile app already has access to the healthcare provider information and patient information, collateral fields may be included with the electronic payment to help the healthcare provider reconcile partial payments to the patient's account.

Figure 9:
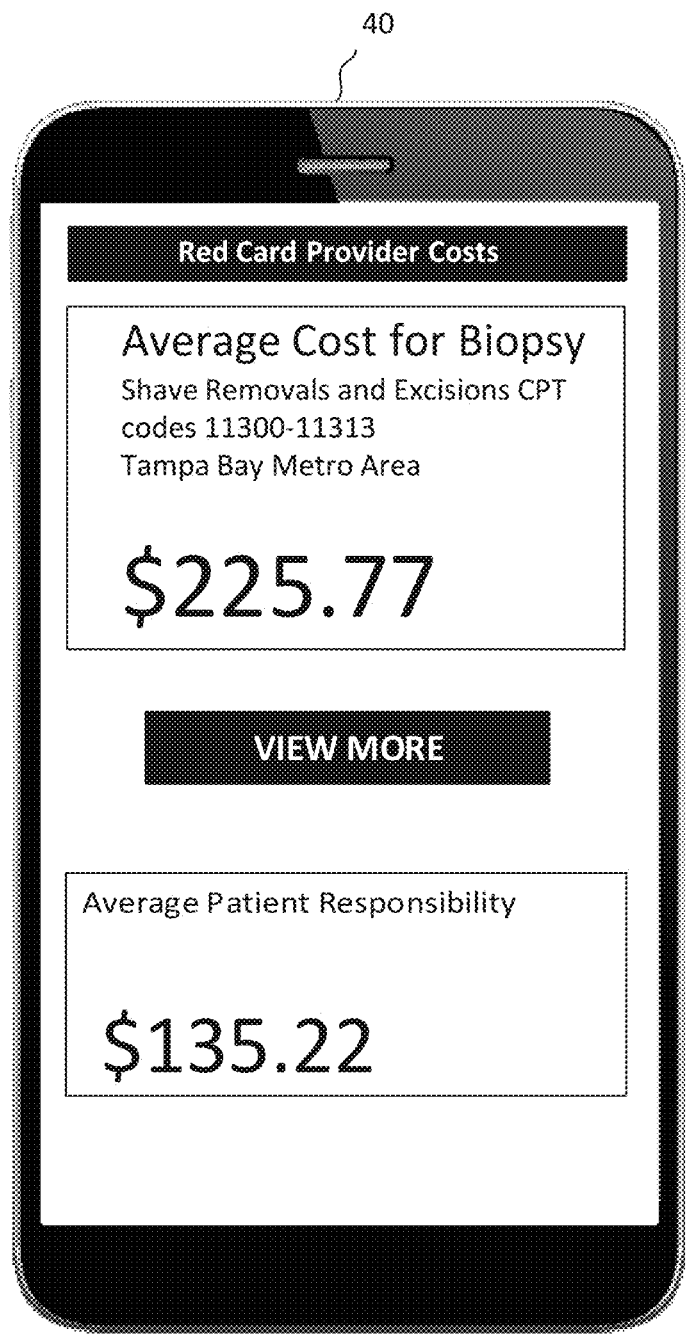
FIG. 9 shows a device GUI displaying an average cost for a known medical procedure according to an embodiment of the invention.

FIG. 9 shows the average cost for a biopsy under CPT codes 11300-11313 for the Tampa Bay metro area. This information is aggregated by processing a plurality of healthcare provider bills and EOBs. The mobile app user can access these statistics which better inform the patient on medical costs. The information will also assist the patient in detecting patient responsibilities that are unusually excessive and may reflect an unintentional error in billing by the healthcare provider.

Figure 10:
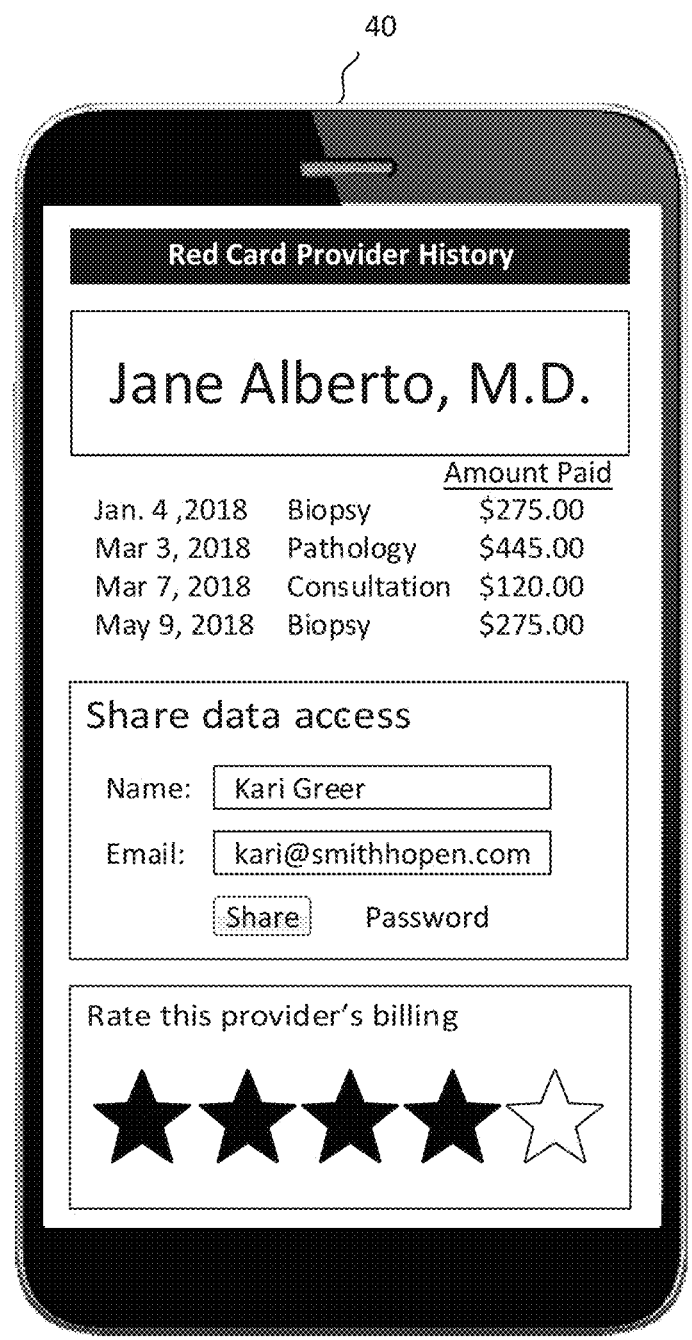
FIG. 10 shows a device GUI display a patient history for a healthcare provider, an interface for sharing access and a rating control according to an embodiment of the invention.

FIG. 10 shows a UI on the mobile app with a number of features. The first is a billing and procedure history for a particular healthcare provider. Should the mobile app user pay through the mobile app, certain bills may be marked "paid" on the UI. The listing may be interactive wherein selecting a line item opens additional detail about the procedure, billing and standardized EOB information aggregated together according to the invention.

Yet another feature shown in FIG. 10 is a control for sharing medical record access to a third party. This may be a friend, family member or additional healthcare provider. The end user inputs at least an email address for the person to which access will be granted. An email is generated with a temporary unique GUID link to a secure account setup interface for the third party to establish access to the patient information. The access may be modified, renewed or revoked by the mobile app user as desired. The mobile app user may also receive notifications when the third party has accessed their records including geolocation data from the IP address used to access the system. For security, access may be denied if a third-party attempts to access the data from outside a geo-fence (e.g., a city, state, country or the like).

Finally, the mobile app user may rate the healthcare provider experience (in this example, giving four of five stars). Additional metrics may be queried beyond "provider billing" such as wait times, scheduling, attentiveness and other aspects of medical interaction.

Figure 11:
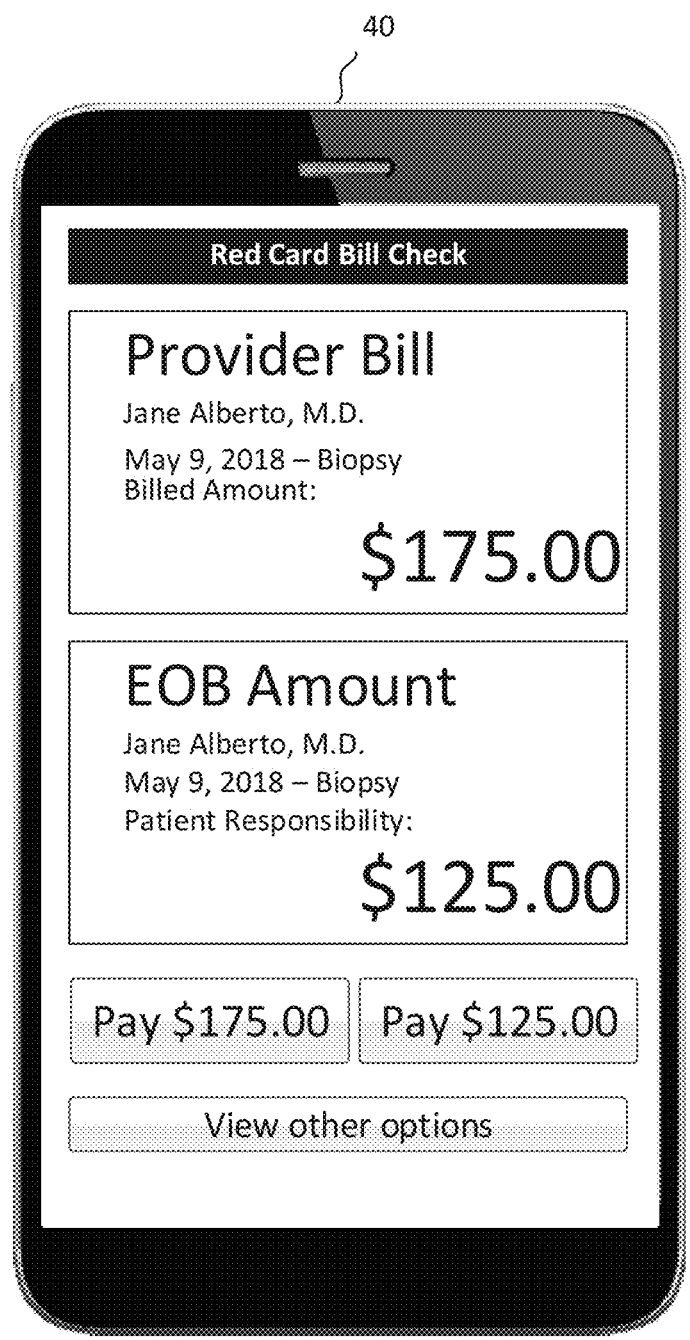
FIG. 11 shows a device GUI display of a discrepancy between a healthcare provider amount due and an EOB-calculated amount due according to an embodiment of the invention.

FIG. 11 shows a $50 difference between a healthcare provider amount due and an EOB-calculated amount. The mobile app automatically creates a first control to authorize payment of the provider amount and a second control to authorize payment of the EOB amount. This provides an option for the healthcare provider to receive payment immediately for an amount not in dispute. It is possible that the greater provider amount is correct. However, a patient is unlikely to voluntarily pay the greater amount without some additional justification. The mobile app may automatically add to a memo line in the electronic payment to the healthcare provider that this partial amount was calculated from the EOB.

An advantage of the invention is not just the payment facilitation, but the reasons behind the payment. Because the system has data from both the provider bill and the standardized EOB data it can relay that along with the payment information to the provider in a string field (e.g., the memo field on an electronically created paper check or a text string field in an electronic payment). For example, the memo field may read "EOB shows $125 pat. respon." Another example would read "partial payment, patient requests add 30 days." By conveying the terms of the payment in a clear and consistent manner, the healthcare provider accounts receivables department may better apply payments and even make adjustments and corrections in follow-up billing. The mobile app may facilitate conveying this information by pre-populating the payment instructions using the standardized EOB data and provider billing data and generating selectable controls that minimize interaction with the UI. For example, instead of requiring the user to type in the payment amount the mobile app UI fills in the text box field with the recommended payment amount. If the mobile app gives the end user payment choices in amount, a plurality of controls with descriptive labels may be generated so that executing one of those options is simply a selection and confirmation. The mobile app takes care of the rest of the process.

HARDWARE AND SOFTWARE INFRASTRUCTURE EXAMPLES

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

GLOSSARY OF CLAIM TERMS

Application means a computer software application executing on a remote or local computer device which may include a workstation, smartphone, tablet, thin client or the like.

End User means a computer user operating a computer software application.

End user does not mean a developer typically having write access to the source code of the application.

Executable instructions means procedures and functions called by computer software.

Explanation of Benefits (EOB) means a statement sent by a health insurance company to covered individuals explaining what medical treatments and/or services were paid for on their behalf Geolocation means the identification or estimation of the real-world geographic location of a computer user by associating a geographic location with the Internet Protocol (IP) address, MAC address, RFID, hardware embedded article/production number, embedded software number (such as UUID, Exif/IPTC/XMP or modern steganography), Wi-Fi positioning system, or device GPS coordinates.

Healthcare Provider means a doctor of medicine or osteopathy, podiatrist, dentist, chiropractor, clinical psychologist, optometrist, nurse practitioner, nurse-midwife, or a clinical social worker who is authorized to practice by a governing regulatory body. For the purposes of this invention, healthcare provider also includes hospitals, clinics, outpatient facilities, prosthetics, medical suppliers and similar entities that send bills for healthcare-related expenses that may be covered by insurance.

Image means a digital picture represented in raster or vector format. Common raster formats include JPG, TIFF, PNG and BMP. Common vector formats include SVG, EPS and AI.

Insurance means includes insurance companies, health maintenance organizations (HMOs), preferred provider organizations (PPOs), or government agencies such as Medicare, Medicaid, or the like.

Memory array means memory accessible by a computing device which stores and loads an operating system and software applications.

Mobile device means a portable computing device such as a smartphone, tablet and notebooks computer, typically handheld and communicatively coupled to a global computer network through WIFI and/or cellular connections.

Optical camera means a camera that captures photographs in digital memory using a CCD or CMOS.

Optical character recognition (OCR) means recognition of printed or written text characters by a computer. This involves photo-scanning of the text character-by-character, analysis of the scanned-in image, and then translation of the character image into character codes, such as ASCII, commonly used in data processing. OCR also includes processing and identification of the document layout both for the context of the character strings processed therein and as a means to identify the origin of the document.

Patient identity means the unique identity of the patient which may be resolved by member ID, subscriber ID, social security number, name, date of birth, address, email address or the like.

Processor means an electronic circuit which performs operations on some external data source, usually memory or some other data stream.

Provider identity means the unique identity of the healthcare provider which may be represented by tax identification number, national provider identifier, practice name, street address or the like.

Software module means a software application or collection of software applications located on one or more computer processing platforms to perform a function or procedure.

User identity means a unique value for an end user operating a mobile device.

This may be a primary key value such as an integer, GUID, email address, user name string or the like.

Validation means checking the accuracy or acceptability of the healthcare provider bill reconciled to the EOB data. This may be a Boolean value requiring an exact match, a fixed threshold value, or a variable threshold value. By way of example, validation may be satisfied by a reconciliation within $10, within 5% or may contain user or application-defined logic such as requiring exact amounts over $1,000 or by type of procedure or medical expense.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A method of standardizing healthcare records to analyze the validity of a healthcare provider's unpaid bill, comprising:

providing remote access to insurance providers over a first network so any one of the insurance providers can provide adjudicated claims data to a claims conversion server, wherein the one of the insurance providers provides the adjudicated claims data in a non-standardized format;

converting, by a claims conversion server, the non-standardized adjudicated claims data into a standardized format;

storing the standardized adjudicated claims data in an EOB database in the standardized format;

providing remote access to users over a second network so any one of the users can upload the healthcare provider's unpaid bill through a graphic user interface on a mobile device;

automatically identifying the one user's identity;

initiating a bill validation module, wherein the bill validation module executes the following steps:

automatically identifying from the healthcare provider's unpaid bill one or more of the following: a healthcare provider's identity, an amount due, and a service date;

automatically accessing the EOB database and performing a scoring algorithm to determine if any of the standardized adjudicated claims data in the EOB database contains enough similarities to the one user's identity, the healthcare provider's identity, the amount due, or the service date to exceed a predetermined scoring threshold;

responsive to one of the standardized adjudicated claims data exceeding the predetermined scoring threshold, automatically generating a message containing a confirmation that the healthcare provider's unpaid bill has been validated; and transmitting the message to the one user over the second network, so that the one user has immediate access to up-to-date payment information.

2. The method of claim 1, wherein the one user's identity is identified by one or more of a name, a user login, a social security number, a date of birth, or a zip code.

3. The method of claim 1, further including receiving the healthcare provider's unpaid bill as a first digital image taken with a digital camera and converting the first digital image to a digital dataset of alphanumeric characters, wherein the digital dataset includes the healthcare provider's identity, the amount due, and the service date.

4. The method of claim 1, further comprising displaying on the one user's mobile device a comparison of the amount of the healthcare provider's unpaid bill that the one user is required to pay as calculated by the healthcare provider and the amount of the healthcare provider's unpaid bill that the one user is required to pay as reported by standardized adjudicated claims data.

5. The method of claim 4, further comprising displaying a selectable control to pick whether to pay the amount of the healthcare provider's unpaid bill as calculated by the healthcare provider or the amount of the healthcare provider's unpaid bill that the one user is required to pay as reported by standardized adjudicated claims data.

6. The method of claim 1, further comprising:

responsive to none of the standardized adjudicated claims data exceeding the predetermined scoring threshold, automatically generating a message containing an explanation that the healthcare provider's unpaid bill has not been validated by the standardized adjudicated claims data; and transmitting the message to the one user over the second network, so that the one user has immediate access to up-to-date payment information.

7. A method of standardizing healthcare records to analyze the validity of a healthcare provider's unpaid bill, comprising:

providing remote access to insurance providers over a first network so any one of the insurance providers can provide adjudicated claims data to a claims conversion server, wherein the one of the insurance providers provides the adjudicated claims data in a non-standardized format;

converting, by a claims conversion server, the non-standardized adjudicated claims data into a standardized format;

storing the standardized adjudicated claims data in an EOB database in the standardized format;

receiving a first digital image taken with a digital camera and digitally sent from a patient's mobile device, the first digital image comprising the healthcare provider's unpaid bill for a patient;

converting the first digital image to a digital dataset of alphanumeric characters, wherein the digital dataset includes a healthcare provider's identity, an amount due, and a service date;

identifying a patient's identity;

initiating a bill validation module, wherein the bill validation module executes the following steps:

automatically accessing the EOB database and retrieving standardized adjudicated claims data in the EOB database that corresponds to the patient's identity;

automatically matching the digital dataset of the healthcare provider's unpaid bill to a claim in the retrieved standardized adjudicated claims data that corresponds to the patient's identity;

automatically validating the amount due listed on the healthcare provider's unpaid bill by comparing the amount due listed on the healthcare provider's unpaid bill against an amount that the patient must pay out-of-pocket provided in the matched claim;

responsive to validating the amount due listed on the healthcare provider's unpaid bill, automatically generating a message containing a confirmation that the healthcare provider's unpaid bill has been validated;

transmitting the message to the patient, so that the patient has immediate access to up-to-date payment information; and providing, on the graphic user interface, the patient with an option to initiate a digital payment to the healthcare provider.

8. The method of claim 7, wherein the bill validation module further includes:

automatically identifying from the healthcare provider's unpaid bill a healthcare provider's identity, an amount due, and a service date;

performing a scoring algorithm when validating the amount due listed on the healthcare provider's unpaid bill, wherein the scoring algorithm calculates whether any of the standardized adjudicated claims data in the EOB database contains enough similarities to the healthcare provider's identity, the amount due, and the service date to exceed a predetermined scoring threshold to validate the amount due listed on the healthcare provider's unpaid bill;

wherein the step of automatically generating a message containing a confirmation that the healthcare provider's bill has been validated occurs when one of the standardized adjudicated claims data exceeds the predetermined scoring threshold.

9. The method of claim 7, wherein the patient's identity is identified by one or more of a name, user login information, a social security number, a date of birth, or a zip code.

10. The method of claim 7, further comprising displaying on the patient's mobile device a comparison of the amount of the healthcare provider's unpaid bill that the patient is required to pay as calculated by the healthcare provider and the amount of the healthcare provider's unpaid bill that the patient is required to pay as reported by the standardized adjudicated claims data.

11. The method of claim 10, further comprising displaying a selectable control to pick whether to pay the amount of the healthcare provider's unpaid bill as calculated by the healthcare provider or the amount of the healthcare provider's unpaid bill that the patient is required to pay as reported by standardized adjudicated claims data.

12. The method of claim 7, further comprising:
responsive to none of the standardized adjudicated claims data matching the digital dataset, automatically generating a message containing an explanation that the healthcare provider's unpaid bill has not been validated by the standardized adjudicated claims data; and
transmitting the message to the patient, so that the patient has immediate access to up-to-date payment information.

13. A method of standardizing healthcare records to analyze the validity of a healthcare provider's unpaid bill, comprising:
providing remote access to insurance providers over a first network so any one of the insurance providers can provide adjudicated claims data to a claims conversion server, wherein the one of the insurance providers provides the adjudicated claims data in a non-standardized format;
converting, by a claims conversion server, the non-standardized adjudicated claims data into a standardized format;
receiving a first digital image taken with a digital camera and digitally sent from a patient's mobile device, the first digital image comprising the healthcare provider's unpaid bill for a patient;
converting the first digital image to a digital dataset of alphanumeric characters, wherein the digital dataset includes a healthcare provider's identity, an amount due, and a service date;
identifying a patient's identity;
initiating a bill validation module, wherein the bill validation module executes the following steps:
automatically identifying standardized adjudicated claims data that corresponds to the patient's identity;
automatically matching the digital dataset of the healthcare provider's unpaid bill to a claim in the retrieved standardized adjudicated claims data that corresponds to the patient's identity;
automatically validating the amount due listed on the healthcare provider's unpaid bill by comparing the amount due listed on the healthcare provider's unpaid bill against an amount that the patient must pay out-of-pocket provided in the matched claim;
responsive to validating the amount due listed on the healthcare provider's unpaid bill, automatically generating a message containing a confirmation that the healthcare provider's unpaid bill has been validated; and
transmitting the message to the patient, so that the patient has immediate access to up-to-date payment information.

14. The method of claim 13, further including providing, on a graphic user interface, the patient with an option to initiate a digital payment to the healthcare provider.

15. The method of claim 13, further including storing the standardized adjudicated claims data in an EOB database in the standardized format.

16. The method of claim 13, wherein the bill validation module further includes:
performing a scoring algorithm when validating the amount due listed on the healthcare provider's unpaid bill, wherein the scoring algorithm calculates whether any of the standardized adjudicated claims data in the EOB database contains enough similarities to the healthcare provider's identity, the amount due, and the service date to exceed a predetermined scoring threshold to validate the amount due listed on the healthcare provider's unpaid bill;
wherein the step of automatically generating a message containing a confirmation that the healthcare provider's bill has been validated occurs when one of the standardized adjudicated claims data exceeds the predetermined scoring threshold.

17. The method of claim 13, wherein the patient's identity is identified by one or more of a name, a social security number, a date of birth, or a zip code.

18. The method of claim 13, further comprising displaying on the patient's mobile device a comparison of the amount of the healthcare provider's unpaid bill that the patient is required to pay as calculated by the healthcare provider and the amount of the healthcare provider's unpaid bill that the patient is required to pay as reported by the standardized adjudicated claims data.

19. The method of claim 18, further comprising displaying a selectable control to pick whether to pay the amount of the healthcare provider's unpaid bill as calculated by the healthcare provider or the amount of the healthcare provider's unpaid bill that the patient is required to pay as reported by standardized adjudicated claims data.

20. The method of claim 13, further comprising:
responsive to none of the standardized adjudicated claims data matching the digital dataset, automatically generating a message containing an explanation that the healthcare provider's unpaid bill has not been validated by the standardized adjudicated claims data; and
transmitting the message to the patient, so that the patient has immediate access to up-to-date payment information.

* * * * *